United States Patent [19]

Haynes

[11] Patent Number: 5,312,368
[45] Date of Patent: May 17, 1994

[54] PROTECTIVE SHIELD FOR HYPODERMIC SYRINGE

[75] Inventor: Don A. Haynes, Okemos, Mich.

[73] Assignee: Haynes-Miller, Inc., Okemos, Mich.

[21] Appl. No.: 65,807

[22] Filed: May 21, 1993

[51] Int. Cl.⁵ .............................................. A61M 5/32
[52] U.S. Cl. ...................................... 604/192; 604/263
[58] Field of Search ................ 604/110, 187, 192, 263

[56] References Cited

U.S. PATENT DOCUMENTS

| | | | |
|---|---|---|---|
| 4,664,259 | 5/1987 | Landis | 604/192 X |
| 4,966,591 | 10/1990 | Yuen | 604/192 |
| 5,232,455 | 8/1993 | Hollister | 604/263 X |

FOREIGN PATENT DOCUMENTS 2618685  2/1989  France ................. 604/192

Primary Examiner—John D. Yasko
Attorney, Agent, or Firm—Howard & Howard

[57] ABSTRACT

A shield for protecting the needle of a syringe. The shield has a connector for connecting the shield to the syringe with the connector preferably being generally annular and adapted to slip fit over the base of the needle, unless the syringe is formed with a needle, then the connector body would fit over the end of the syringe. The shield includes at least one protective arm hingedly mounted upon the connector and pivotable between first and second positions. The first position is the normal position wherein the protective arm conceals the needle and the second position corresponds to the protective arm being pivotally displaced to expose the needle. The arm is automatically biased to the first position so that the needle is normally and automatically concealed.

6 Claims, 3 Drawing Sheets

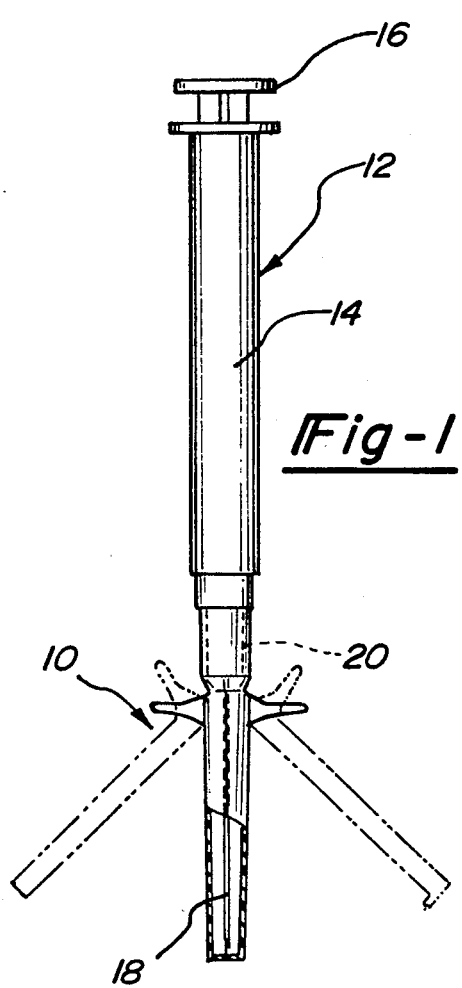
Fig-1
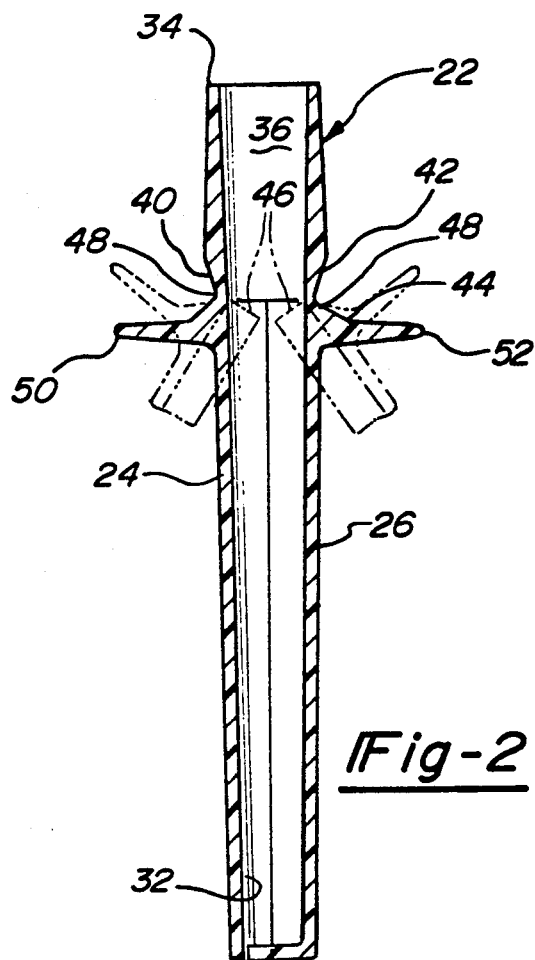
Fig-2
Fig-2A
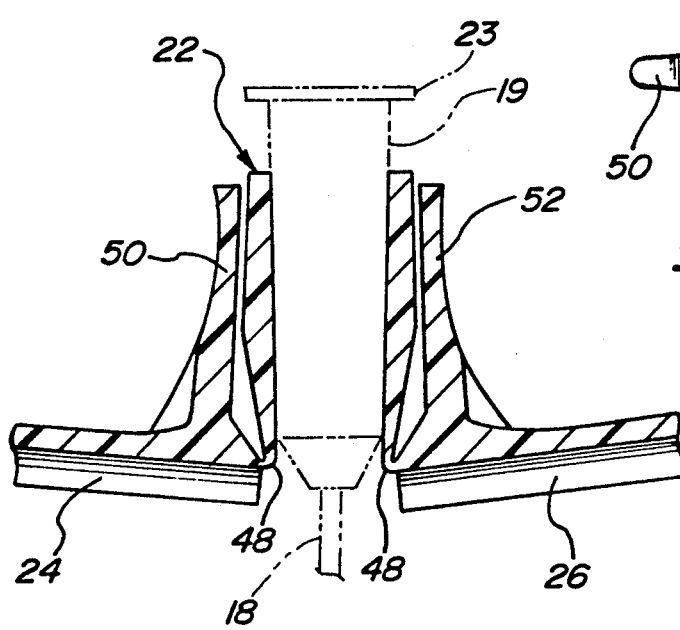
Fig-3

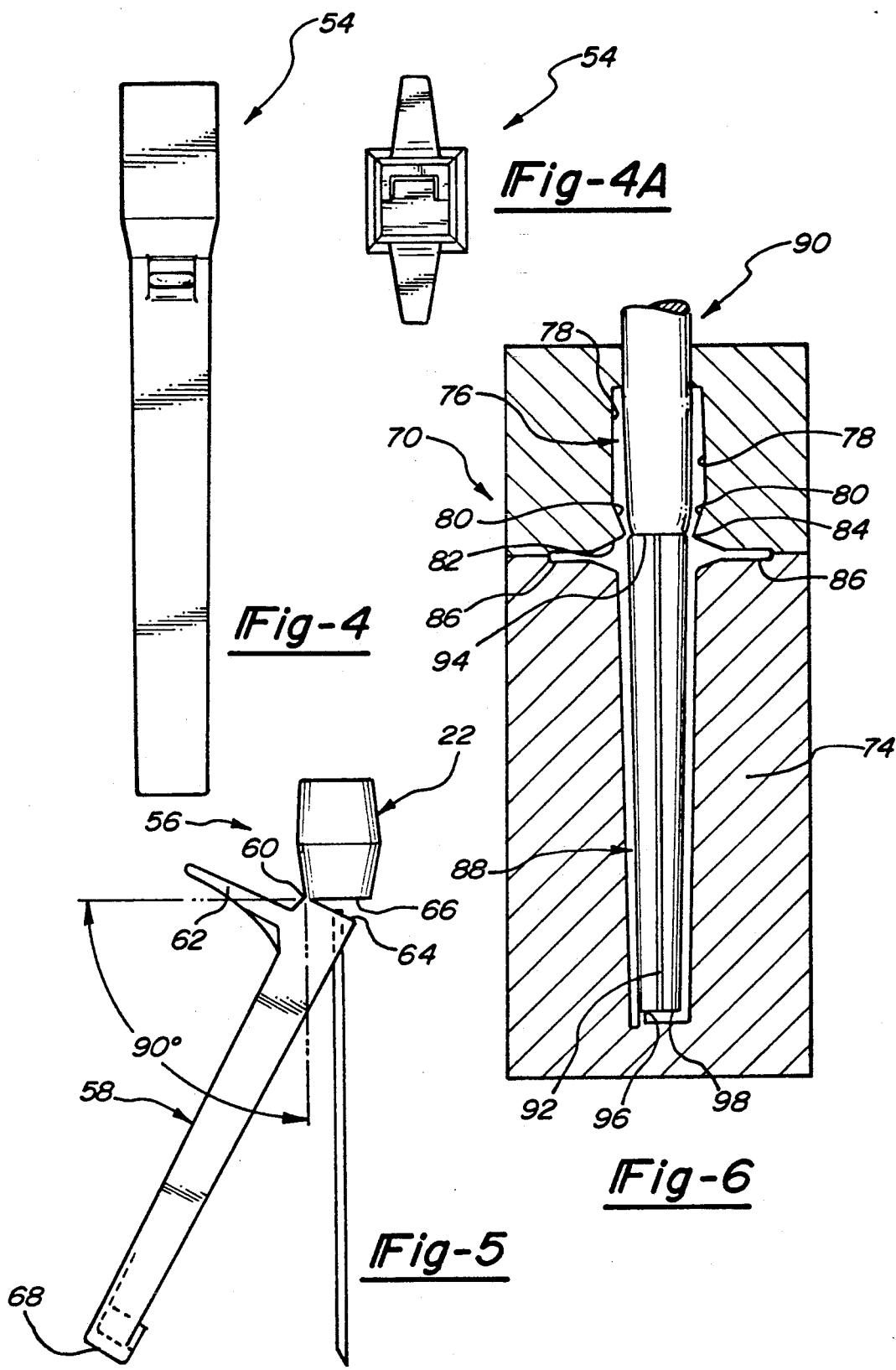

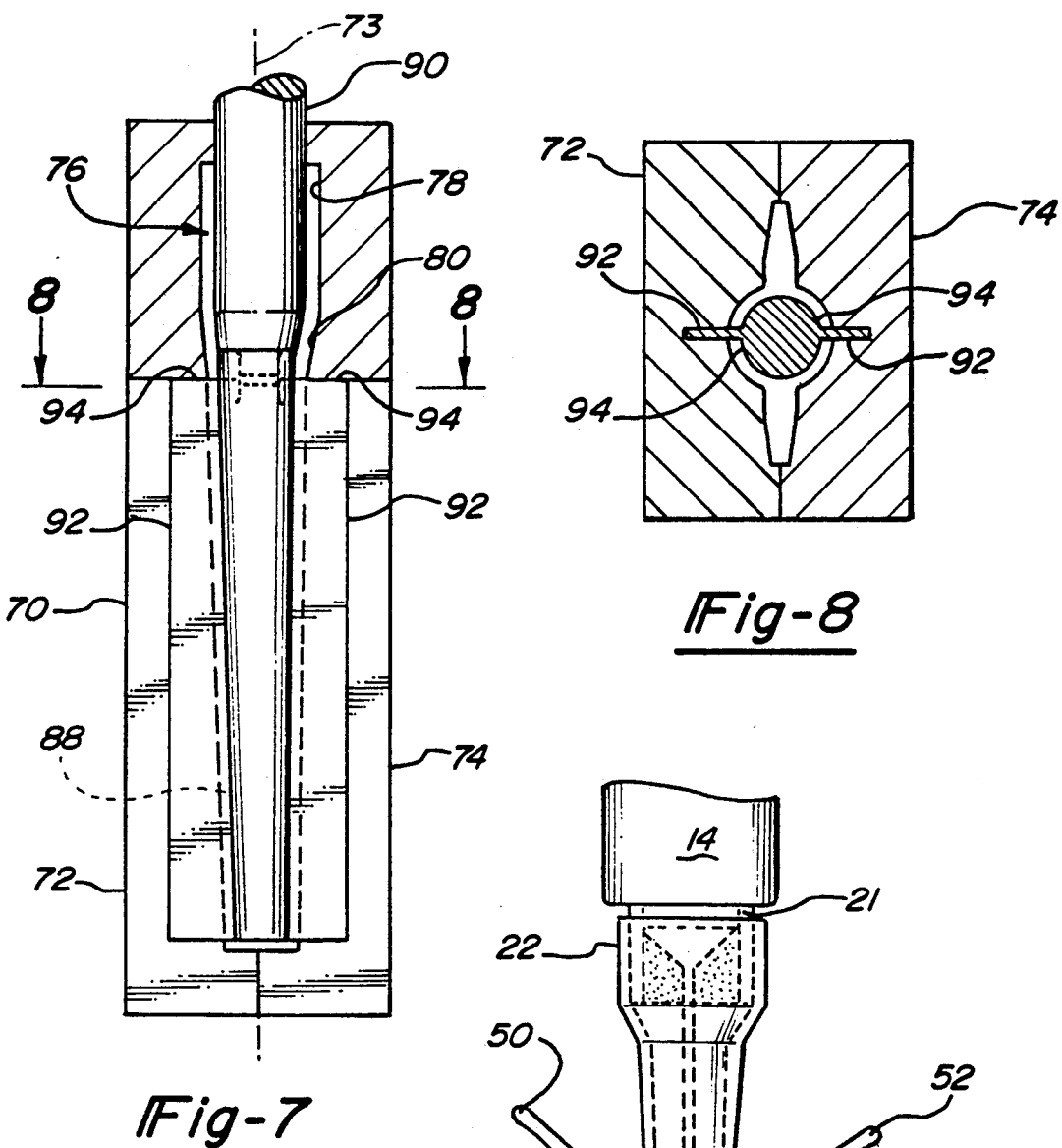

PROTECTIVE SHIELD FOR HYPODERMIC SYRINGE

BACKGROUND OF THE INVENTION

The present invention relates to a protective device for a hypodermic syringe and more importantly to a protective device that normally and automatically envelopes the needle of a hypodermic syringe.

There have been may attempts at making protective devices to protect users of hypodermic syringes from inadvertent punctures. This has become a particular concern now with the consequences of AIDS. To applicants knowledge, these prior attempts have all been attempts to conceal the needle during transport, either before or after use. The known devices typically require manual movement of a sheath or similar protective member to expose the needle so that the needle can be used and once an injection is made, manual movement of the sheath to conceal the needle so that the needle can be disposed of without inadvertent puncture.

These known sheaths do not address the danger of an exposed needle during the period just prior to use through just after the injection during which the sheath does not conceal the needle. For example, there is the possibility that during the injection the patient will jump and the needle will be dropped or it may be propelled into the air. The applicant is aware of instances where the needle has been propelled and inadvertently stuck the individual giving the injection.

The only protective sheaths that the applicant is aware of that provide protection during the period of use employ a coil spring to automatically extend the sheath. These protective sheaths either require too much manipulation or are too costly.

SUMMARY OF THE INVENTION

The protective devise of the present invention overcomes the above problems found in known devices by providing an inexpensive automatic shield that normally conceals the needle of a hypodermic syringe and has to be manually biased to expose the needle.

The protective shield of the preferred embodiment of the present invention is a clam shell type design having two members that are normally closed about the needle of the syringe. The shield includes a mounting collar that is preferably slip fit over the end of the base of the needle or syringe body. The two members are hingedly connected to the mounting collar so that they can pivot with respect to the needle. In order to expose the needle, the two members are pivoted about the hinge with respect to one another. In the disclosed embodiment, there are finger grips provided to facilitate the pivoting of the two members. The hinge is formed so that it biases against the members, biasing them back to the normal position corresponding to the closed position. In this way, due to the bias, the two members are automatically returned to the concealing position if the manual applied force on the members is released, as for example if the needle and syringe is dropped or knocked from the user's hand.

As should be appreciated by one of ordinary skill in the art, the sheath would not need to be removed from the needle for use which greatly reduces the potential for contamination. Further, as soon as the needle is inserted, the force to open the sheath can be released and the two halves of the sheath, because of the resilient memory of the material used, will automatically close the two halves against the skin of the patient. Since there are only a few ounces of force needed to close the two members, the patient feels no discomfort. When the needle is removed, by purpose or accident, the sheath snaps shut, covering the needle.

The present application also discloses an alternative embodiment of the present invention wherein there is only one pivotal member that has an open side for exposing the needle. The one member or arm is pivoted against the bias of the hinge in a manner similar to the above clam-type shield.

There is also disclosed a preferred method of making the shield of the present invention.

BRIEF DESCRIPTION OF THE DRAWINGS

FIG. 1 is a plan view of the protective shield of the present invention mounted upon the base of the needle attached to a hypodermic syringe.

FIG. 2 is a plan view of the protective shield of the present invention.

FIG. $2^1$ is an end view of the preferred embodiment of the present invention.

FIG. 3 is a plan view of the protective shield attached to the base of the needle of the present invention in the exposed position.

FIG. 4 is a plan view of a second embodiment of the present invention.

FIG. $4^1$ is an end view of the shield illustrated in FIG. 4.

FIG. 5 is a further embodiment of the shield of the present invention.

FIG. 6 is a top view of the preferred mold for injection molding the shield of the present invention with the top of the mold removed.

FIG. 7 is a cut away side view of the preferred mold for injection molding of the shield.

FIG. 8 is a view taken along line 8—8 of FIG. 7.

FIG. 9 is a view of the protective shield mounted to the end portion of a hypodermic syringe.

DETAILED DESCRIPTION OF THE PREFERRED EMBODIMENT

The protective hypodermic needle shield of the present invention is shown generally at 10 in FIG. 1. The shield 10 is mounted upon the base 19 of needle 18 on a standard hypodermic syringe 12 (see FIG. 3). The syringe 12 includes a barrel 14 which receives a plunger 16 at one end and has a hypodermic needle 18 attached at the opposite end. It is to be understood that syringe as used in this application, refers broadly to the barrel, needle and base of needle, and any hub or end portion of the barrel. The disclosed hypodermic syringe includes a coupling 20 that couples the base 19 of needle 18 to the barrel 14. The coupling 20 allows the needle 18 to be removed from barrel 14. It should be understood that the needle 18 could be integrally formed to the barrel 14 without affecting the application of the present invention. It is also within the scope of this invention that the protective shield 10 can be mounted to the end of the syringe 12 adjacent to the needle 18 or mounted to the barrel 14 of the syringe 12.

With reference to FIG. 2, the shield 10 of the present invention is shown in greater detail. The shield 10 has a connector body 22 which slide on the base 19 of the needle 18. The shield is generally installed on the needle at the time of assembly. With reference to FIG. 3, Luer-Lok tabs 23 are illustrated for example as a known method of attaching the needle 18 to barrel 14. Tabs 23 molded are into base 19 of needle 18 onto which the connector body 22 slides. The vertical projections normally found on the base 19 of the needle are not illustrated, but those of ordinary skill in the art will appreciate that these projections are received within grooves to receive the projections to prevent slipping. Syringes with a slip-tip would not require the grooves. As should be appreciated, other methods of preventing the sheath of the present invention from slipping will become apparent to those of ordinary skill in the art and are considered to be within the scope of this invention.

As illustrated in FIG. 2, the protective arms 24 and 26 each have a semi-circular cross-section. The arms 24 and 26 are illustrated in the closed position wherein the arms mate to form a circular cross-section with a closed end 30 to envelope the needle 18. The closed position is the normal position for the arms 24 and 26 so that the needle 18 normally remains enveloped preventing inadvertent puncture by the needle 18.

The sheath is generally tubular in shape and has a slight taper from its top 34 to end portion 30. The inner diameter 36 of connector body 22 is made to fit the outer diameter of the base 19 of needle 18, or the end portion 21 of the barrel 14 if there is no coupling 20 or the barrel 14 if it is desired to mount shield 10 to the barrel 14. This permits the connector body 22 to be slip fit onto syringe 12.

As disclosed, the arm 24 terminates in an end face 28. The arm 26 terminates in an inwardly turned end portion 30 that abuts against the inner wall 32 of arm 24 to cover the terminal end of the needle 18. In this way, the needle is fully enclosed.

As stated above, the arms 24 and 26 are normally in the closed position as illustrated by the solid lines in FIG. 2. To expose the needle 18, the arms 24 and 26 must be pivoted with respect to the syringe 12. The pivoting action is shown by the phantom lines in FIGS. 1 and 2. In order for the arms 24 and 26 to pivot, the sheath has a reduced outer diameter at 40. In the embodiment illustrated in FIGS. 1 and 2, the reduced diameter is defined by intersecting angled walls 42 and 44 which intersect at the top 46 of the arms 24 and 26.

The reduced diameter 40 defines flexible hinges 48 between the arms 24 and 26 and the connector 22 which bias arms 24 and 26 to their closed position to conceal the needle 18. Protruding outwardly from the arms 24 and 26 are finger grips 50 and 52. In the preferred embodiment of the invention, the finger grips 50 and 52 are integrally formed with the remainder of the shield 10. As illustrated in FIGS. 1 and 2, the top of the finger grips define the angled wall 44 of reduced portion 40.

With reference to FIG. 3, the fully open position of sheath 10 is illustrated. The arms 24 and 26 are generally perpendicular to the syringe 12 fully exposing the needle 18. In this position the fingers 50 and 52 are pressed by the user against the connector body 22. It should be understood that the hinges 48 are biasing the arms 24 and 26 to the normally closed position as shown in FIGS. 1 and 2. The user is responsible for holding the arms 24 and 26 in the illustrated position to expose the needle 18. If the user releases the fingers 50 and 52 the arms 24 and 26 will automatically be forced back to the closed position concealing the needle 18. To facilitate the users ability to hold the arms 24 and 26, finger grips 50 and 52 are slightly concave to conform to the user's finger and thumb. Knurling can also be used to facilitate gripping.

With reference to FIG. 4, a further embodiment of the shield 10 of the present invention is shown generally at 54. This embodiment is generally the same as the previous embodiment, except that it has a square cross-section, see FIG. $4_1$ as opposed to a circular cross-section, see FIG. $2_1$. It should be understood by those of ordinary skill in the art that the cross-section could have other geometric shapes, for example it could have a triangular cross-section with the arm 24 being generally flat in cross-section and the arm 26 having a triangular cross-section.

With reference to FIG. 5, another embodiment of the shield of the present invention is shown generally at 56. As before, the shield 56 has a connector body 22 for a slip fit connection to the base 19 of needle 18. In this embodiment, instead of two arms 24 and 26, there is a single arm 58 which is hinged at 60 to connector body 22. One side of arm 58 has an opening wide enough to let the needle 18 pass through during movement. A single finger 62 is used to pivot the arm 58 from the normally closed position, in which the needle 18 is covered, to the fully exposed position, in which the needle is fully exposed. The arm 58 is generally perpendicular to the needle 18 in the fully exposed position. As before, the hinge 60 resists efforts to pivot the arm 58 from the normally closed position, i.e. generally parallel to the needle 18, to the fully exposed position, i.e. generally perpendicular to needle 18.

As can be appreciated, the arm 58 will automatically return to the closed position. In this embodiment the top 64 of arm 58 extends across the base 66 of connector 22. In the previous embodiment, the tops 46 of each arm 24 and 26 extended only about one-half the distance across the base of the connector 22. Additionally, in this embodiment the end 68 extends at a generally right angle with respect to the arm 58 to cover the end of needle 18 when the arm is in the closed position.

With reference to FIG. 6, a preferred mold and method of making the sheath 10 of the present invention will be described. The mold is shown generally at 70. The mold has two halves, a top half 72 and a bottom half 74 that can be separated along a longitudinally extending part line 73. The mold halves 72 and 74 form cavities which define the exterior of the sheath 10. The cavity 76, formed by the two molds 72 and 74, has a first inside diameter 78 that tapers slightly to an inwardly angled portion 80 that corresponds to wall 42. The inwardly angled portion 80 ends at an apex 84 which begins the outwardly angled portion 82 that corresponds to the wall 44 that corresponds to wall 44. The angled portion 82 extends to a generally perpendicular cavity 86 relative to the center line that defines the fingers 50 and 52. The perpendicular cavity 86 is formed on both the top half 72 and bottom half 74 of the mold 70. Extending into the top half 72 and the bottom half 74 is a tapered cavity 88 that defines the outer surface of the arms 24 and 26.

A core insert 90 is adapted to be inserted into the cavities 72 and 74. Core insert 90 defines the interior of the sheath 10. The insert 90 is slightly tapered along its length. To define the two arms 24 and 26, longitudinal blades 92 are inserted project in from the molds 72 and 74 on opposed sides of the insert 90. The blades 92 extend in to the insert 90, which has shallow grooves to accept them. As should be appreciated, the blades will form a line of separation on both sides of the arms 24 and 26 when they are molded. A second pair of smaller blades 94 are inserted or projected in from the molds 72 and 74, which are generally perpendicular to the blades 92. It should be appreciated that the blades 94 will have an interior shape that is the same as the exterior shape of core insert 90. The blades 94 define the tops 46 of the arms 24 and 26.

In the preferred embodiment, blades 94 are inserted in grooves cut in the top half 72 and bottom half 74. Also, blades 92 are inserted in grooves cut in the top half 72 and bottom half 74. The blades 92 abut blades 94 when closed. Shallow grooves are cut in insert 90 to accept the blades 92 and 94 when closed. With insert 90 in place to mold sheath 10, the top 72 and bottom 74 of the mold 70 are connected together by means well known to those of ordinary skill in the art. An engineered material is then injected into the cavity to form sheath 10. Once the material has obtained the shape of the cavity and sets, molds 72 and 74 are separated to enable the sheath 10 to be removed. It should be appreciated that the material to be used for the sheath 10 will require the necessary physical and mechanical properties such that the needle will automatically be protected by arms 24 and 26 after release of fingers 50 and 52 which control exposure of needle 18. It is believed that a plastic such as polypropylene will be acceptable, but it is believed that other spring type material would be acceptable.

It should be understood that the other embodiments could be molded in a similar mold with slight variations to the mold. The mold of the preferred embodiment permits sheaths to be quickly and inexpensively molded.

Although the present invention has been described in detail with reference only to the presently preferred embodiments, it will be appreciated by those of ordinary skill in the art that various modifications can be made without departing from the invention. Accordingly, the invention is to be limited only by the following claims.

What is claimed is:

1. A shield for protecting the needle of a syringe, said shield comprising:
   a connector for connecting the shield to the base of needle, said connector being generally annular and adapted to slip fit over the base of the needle;
   a pair of protective arms hingedly mounted upon said connector;
   biasing means normally biasing said arms to a closed position wherein said arms are adjacent to one another to form an enclosure for enclosing said needle of said syringe, said protective arms being manually displaceable with respect to one another against the bias of said biasing means to expose said needle;
   said protective arm and said connector being integrally formed as a one-piece unit, and said biasing means being defined by a notch formed between said protective arm and said connector, also as part of said one-piece unit, to form a resilient hinge between said protective arms and said connector.

2. The shield of claim 1, further including control grips extending outwardly from said protective arms, said control grips being adapted to be grasped by a user to manually displace said protective arms to expose said needle.

3. The shield of claim 2, wherein said control grips extend at about a 90 degree angle with respect to said protective arms.

4. The shield of claim 2, wherein said control grips include a knurled surface to facilitate engagement by a user.

5. The shield of claim 1, wherein said protective arms are generally convex.

6. The shield of claim 1, wherein at least one of said protective arms has an end portion that covers the end of said needle.

* * * * *